US006837854B2

(12) United States Patent
Moore et al.

(10) Patent No.: US 6,837,854 B2
(45) Date of Patent: Jan. 4, 2005

(54) METHODS AND SYSTEMS FOR USING REFERENCE IMAGES IN ACOUSTIC IMAGE PROCESSING

(75) Inventors: Thomas L. Moore, Livermore, CA (US); Robert Henry Barter, Oakland, CA (US)

(73) Assignee: Barbara Ann Karmanos Cancer Institute, Detroit, MI (US)

( * ) Notice: Subject to any disclaimer, the term of this patent is extended or adjusted under 35 U.S.C. 154(b) by 42 days.

(21) Appl. No.: 10/323,866

(22) Filed: Dec. 18, 2002

(65) Prior Publication Data

US 2004/0122313 A1 Jun. 24, 2004

(51) Int. Cl.[7] .................................................. A61B 8/00
(52) U.S. Cl. ....................................................... 600/437
(58) Field of Search ................................. 600/407–472; 606/1, 79, 80, 96, 60, 61, 62, 104, 129, 130

(56) References Cited

U.S. PATENT DOCUMENTS

| | | |
|---|---|---|
| 3,154,067 A | 10/1964 | Stenstrom et al. |
| 3,881,466 A | 5/1975 | Wilcox |
| 3,886,489 A | 5/1975 | Jones |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,222,274 A | 9/1980 | Johnson |
| 4,317,369 A | 3/1982 | Johnson |
| 4,515,165 A | 5/1985 | Carroll |
| 4,542,744 A | 9/1985 | Barnes et al. |
| 4,564,019 A | 1/1986 | Miwa |
| 4,662,222 A | 5/1987 | Johnson |
| 4,671,256 A | 6/1987 | Lemelson |
| 4,722,056 A * | 1/1988 | Roberts et al. ............ 606/130 |
| 4,855,911 A | 8/1989 | Lele et al. |
| 4,858,124 A | 8/1989 | Lizzi et al. |
| 4,917,096 A | 4/1990 | Engelhart et al. |
| 4,941,474 A | 7/1990 | Pratt, Jr. |
| 5,003,979 A | 4/1991 | Merickel et al. |
| 5,029,476 A | 7/1991 | Metala |
| RE33,672 E | 8/1991 | Miwa |
| 5,143,069 A | 9/1992 | Kwon |
| 5,158,071 A | 10/1992 | Umemura et al. |
| 5,179,455 A | 1/1993 | Garlick |
| 5,212,571 A | 5/1993 | Garlick et al. |

(List continued on next page.)

FOREIGN PATENT DOCUMENTS

| | | |
|---|---|---|
| AU | A-34432/95 | 2/1996 |
| EP | 0 351 610 A2 | 1/1990 |
| EP | 0 538 241 B1 | 4/1993 |
| EP | 0 538 241 A2 | 4/1993 |
| EP | 0 284 055 B1 | 9/1993 |
| EP | 0 609 922 A2 | 8/1994 |
| EP | 0 661 029 A1 | 7/1995 |
| EP | 0 774 276 A2 | 5/1997 |

OTHER PUBLICATIONS

Andre, et al. "A New Consideration of Diffraction Computed Tomography for Breast Imaging: Studies in Phantoms and Patients" *Acoustical Imaging*, J.P. Jones, Plenum Press, New York (1995), pp. 379–390.

(List continued on next page.)

*Primary Examiner*—Ali Imam
(74) *Attorney, Agent, or Firm*—Townsend and Townsend and Crew LLP

(57) ABSTRACT

A method and system of examining tissue are provided in which a field, including at least a portion of the tissue and one or more registration fiducials, is insonified. Scattered acoustic information, including both transmitted and reflected waves, is received from the field. A representation of the field, including both the tissue and the registration fiducials, is then derived from the received acoustic radiation.

30 Claims, 7 Drawing Sheets

U.S. PATENT DOCUMENTS

| | | | |
|---|---|---|---|
| 5,255,683 A | | 10/1993 | Monaghan |
| 5,260,871 A | | 11/1993 | Goldberg |
| 5,269,309 A | | 12/1993 | Fort et al. |
| 5,280,788 A | | 1/1994 | Janes et al. |
| 5,304,173 A | | 4/1994 | Kittrell et al. |
| 5,318,028 A | | 6/1994 | Mitchell et al. |
| 5,329,817 A | | 7/1994 | Garlick et al. |
| 5,339,282 A | | 8/1994 | Kuhn et al. |
| 5,349,954 A | | 9/1994 | Tiemann et al. |
| 5,394,875 A | * | 3/1995 | Lewis et al. ............ 600/445 |
| 5,413,108 A | | 5/1995 | Alfano |
| 5,415,164 A | | 5/1995 | Faupel |
| 5,433,202 A | | 7/1995 | Mitchell et al. |
| 5,463,548 A | | 10/1995 | Asada et al. |
| 5,465,722 A | | 11/1995 | Fort et al. |
| 5,474,072 A | | 12/1995 | Shmulewitz |
| 5,479,927 A | | 1/1996 | Shmulewitz |
| 5,485,839 A | | 1/1996 | Aida et al. |
| 5,487,387 A | | 1/1996 | Trahey et al. |
| 5,553,618 A | | 9/1996 | Suzuki et al. |
| 5,558,092 A | | 9/1996 | Unger et al. |
| 5,573,497 A | | 11/1996 | Chapelon |
| 5,582,173 A | | 12/1996 | Li |
| 5,588,032 A | | 12/1996 | Johnson et al. |
| 5,588,430 A | * | 12/1996 | Bova et al. ............ 600/429 |
| 5,590,653 A | | 1/1997 | Aida et al. |
| 5,596,992 A | | 1/1997 | Haaland et al. |
| 5,606,971 A | | 3/1997 | Sarvazyan |
| 5,620,479 A | | 4/1997 | Diederich |
| 5,640,956 A | | 6/1997 | Getzinger et al. |
| 5,643,179 A | | 7/1997 | Fujimoto |
| 5,664,573 A | | 9/1997 | Shmulewitz |
| 5,678,565 A | | 10/1997 | Sarvazyan |
| 5,722,411 A | | 3/1998 | Suzuki et al. |
| 5,743,863 A | | 4/1998 | Chapelon |
| 5,762,066 A | | 6/1998 | Law et al. |
| 5,766,129 A | | 6/1998 | Mochizuki |
| 5,797,849 A | | 8/1998 | Vesley et al. |
| 5,800,350 A | | 9/1998 | Coppleson et al. |
| 5,810,731 A | | 9/1998 | Sarvazyan et al. |
| 5,817,025 A | | 10/1998 | Alekseev et al. |
| 5,833,614 A | | 11/1998 | Dodd et al. |
| 5,846,202 A | | 12/1998 | Ramamurthy et al. |
| 5,865,167 A | | 2/1999 | Godik |
| 5,865,743 A | | 2/1999 | Godik |
| 5,891,619 A | | 4/1999 | Zakim et al. |
| 6,002,958 A | | 12/1999 | Godik |
| 6,005,916 A | | 12/1999 | Johnson et al. |
| 6,109,270 A | | 8/2000 | Mah et al. |
| 6,117,080 A | | 8/2000 | Schwartz |
| 6,135,960 A | | 10/2000 | Holmberg |
| 6,235,038 B1 | * | 5/2001 | Hunter et al. ............ 606/130 |
| 2002/0131551 A1 | | 9/2002 | Johnson |

OTHER PUBLICATIONS

Borup, et al. "Nonperturbative Diffraction Tomography Via Gauss–Newton Iteration Applied to the Scattering Integral Equation" *Ultrasonic Imaging*, Academic Press, Inc. (1992) vol. 14, pp. 69–85.

Chelfouh, et al. "Characterization of Urinary Calculi: In Vitro of 'Twinkling Artifact' Revealed by Color–Flow Sonography" *American Journal of Roentgenology* (1998) vol. 171, pp. 1055–1060.

Dean, Stanley R., "The Radon Transform and Some of Its Applications" *Krieger Publishing Company, Malabar, Florida* (1993).

Greenleaf, J.F. "Tissue Characterization with Ultrasound: vol. II: Results and Applications" *CRC Press, Inc., Boca Raton, Florida* , pp. 95–122.

Greenleaf, J.F., et al. "Introduction to Computer Ultrasound Tomography" *Computed Aided Tomography and Ultrasonics in Medicine*, North–Holland, (1970); pp. 125–136.

Greenleaf, J.F., et al. "Mulitdimensional Visualization of Ultrasonic Images" *J. Acoust. Soc. Amer.* vol. 95 (2902) (1994).

Hebden, et al. "Acoustically Modulated Electrical Impedance Tomography" *Proceedings of the SPIE*, vol. 123 (1990); pp. 7–14.

Jellins, J. "Breast Tissue Characterizations" *Tissue Characterization with Ultrasound*, vol. II, CRC Press, (1980) pp. 95–122.

Johnson, et al. "Modeling of Inverse Scattering and Other Tomographic Algorithms in Conjunction with Wide Bandwidth Acoustic Transducer Arrays for Towed or Autonomous Sub–bottom Imaging Systems" *Proceedings of Mastering the Oceans Through Technology, Oceans* Newport, Rhode Island, USA, (Oct. 26–29, 1992), pp. 294–299.

Johnson, et al. "Comparison of Inverse Scattering and Other Tomographic Imaging Algorithms Using Simulated and Tank Data for Modeling Subbottom Imaging Systems" IEEE Oceans '93 Symposium, Nov. 1993, vol. I, pp. 458–492 (1993).

Louvar, et al. "Correlation of Color Doppler Flow in the Prostate with Tissue Microvascularity" *Cancer*, (Jul. 1998) vol. 1:83 (1); pp. 135–140.

Nelson, et al. "Interactive Acquisition, Analysis and Visualization of Sonographic Volume Data" *International Journal of Imaging Systems and Technology* (1997) vol. 8(26), pp. 26–37.

Sehgal, et al. "Visualization of Breast Calcification by Acoustic Resonance Imaging" *Radiology Supplement*, 84th Scientific Assembly and Annual Meeting, Nov. 29–Dec. 4, 1998 presented in McCormick Place, Chicago, Illinois (1998) vol. 209, listing: 1150.

Shi, et al. "Effects of Pressure Changes on Harmonic and Subharmonic Response of US Contrast Microbubbles" 84th Scientific Assembly and Annual Meeting, Nov. 29–Dec. 4, 1998 presented in McCormick Place, Chicago, Illinois (1998) vol. 209, listing: 1154.

Wiskin, et al. "Full Inverse Scattering vs. Born–like Approximation for Imaging in a Stratified Ocean" *Proc. of Engineering in harmony with the Ocean (Oceans '93)*, Victoria, British Columbia, Oct. 1993.

* cited by examiner

METHODS AND SYSTEMS FOR USING REFERENCE IMAGES IN ACOUSTIC IMAGE PROCESSING

STATEMENT AS TO RIGHTS TO INVENTIONS MADE UNDER FEDERALLY SPONSORED RESEARCH OR DEVELOPMENT

The Government has rights in this invention pursuant to U.S. Dept. of Energy Work for Others Agreement L-8420.

BACKGROUND OF THE INVENTION

The present invention relates generally to imaging systems. More particularly, the present invention relates to ultrasound imaging systems.

There are a number of disadvantages associated with various imaging systems that are currently in use, particularly when used for medical applications. For example, a number of imaging techniques, such as x-ray imaging, mammography, and computed tomographic (CT) scans, use ionizing radiation that presents a risk of cell mutation when used medically. Also, CT scans and magnetic resonance imaging (MRI) techniques both involve procedures that are relatively expensive, a factor that by itself acts to some degree to limit their use. A significant disadvantage of methods such as mammography is that they rely on two-dimensional images that may disguise three-dimensional structure information that can be critical for diagnosis.

As an alternative to these imaging technologies, the medical community has looked to ultrasound for providing a safe, low-cost, high-resolution imaging tool. There are, however, significant limitations to conventional ultrasound, which may be used in A or B scanning modes. Such modes are distinguished by the fact that an A scan is purely one dimensional while a B scan produces a two-dimensional image. As a result, imaging applications tend to use ultrasonic B scanning. In such conventional ultrasound analysis, a small array of elements is moved by hand in contact with tissue under study. The array sends out waves that reflect from tissues back to the same array. This arrangement results in two major drawbacks. First, ultrasonic B scans do not provide information on the properties of the materials themselves; rather, they provide information only on the reflectivity of the boundaries between different types of materials. Second, the array is incapable of capturing radiation except that reflected back to the hand-held sensing array. Considerable information exists, however, in the transmitted waves, but this information is neither captured nor used diagnostically in conventional ultrasonic B scans.

An additional limitation to traditional ultrasound techniques is that when an unknown object is examined, it is difficult to determine success criteria for the image construction. Thus, it would be useful to be able to benchmark the image construction process in order to determine when sufficient accuracy or precision has been obtained. Moreover, in the past, it has been difficult to correlate positions of features in an image with the position of the patient. It therefore is desirable to develop methods of judging the accuracy of an ultrasound image against objective criteria and adjusting the image to correlate to those criteria.

Another useful application for ultrasound imaging is analyzing changes in a tissue, for example, by creating multiple ultrasound representations of the tissue, perhaps over the course of several days, weeks, months or years. Such analysis is most beneficial, however, if it can be undertaken from a consistent frame of reference, such that the size and orientation of the tissue and any features therein are consistently depicted in each representation. Thus, in creating an ultrasound representation, it would be desirable to develop a method of comparing multiple ultrasound scans from a consistent frame of reference.

There is thus a need for an apparatus and method that provides improved imaging, particularly as applied to medical applications.

BRIEF SUMMARY OF THE INVENTION

Embodiments of the invention thus provide a method and system for examining tissue that solve certain deficiencies with the prior art. In one embodiment, a field, including the tissue to be examined as well as one or more registration fiducials, is insonified. The insonifying acoustic waves are scattered by the field so that scattered acoustic information, including in some embodiments a mix of reflected and transmitted acoustic waves, is received, producing a data set. A representation of a portion of the tissue is then generated from the data set. The representation includes a depiction of the registration fiducials. The representation may be three dimensional or may comprise a two-dimensional slice through the portion of the tissue. In one embodiment, the representation comprises an image.

In some embodiments, the registration fiducial comprises an object of known acoustic properties. In such an embodiment, the representation might be calibrated to correlate the depicted properties of the object with the object's known properties. In some embodiments, the field may be insonified a plurality of times, generating a plurality of data sets from which a plurality of representations may be generated. In such an embodiment, the registration fiducials might comprise a plurality of fiducial markers. The relative positions of the plurality of fiducial markers in the representations can be correlated, allowing a feature of the tissue to be localized in the representations. The methods described above may be implemented with a computer program embodied in a computer-readable storage medium.

Another embodiment of the invention is a system for examining tissue, including a sensor system. The sensor system includes a plurality of acoustic transmission elements and acoustic receiving elements disposed to surround a portion of the tissue being examined. The sensor system also includes one or more registration fiducials. The system may also have a control system, including a controller that controls the acoustic transmission elements and the acoustic receiving elements to insonify the field, receive scattered acoustic information and produce a data set from the received acoustic information. The system also might have a processing system with a processor that generates one or more representations of the field from the data sets produced by the control system, such representations depicting at least a portion of the tissue insonified as well as the registration fiducials. In some embodiments, the processor might also process the representations to correlate the depictions of the registration fiducials with the fiducials' actual properties.

BRIEF DESCRIPTION OF THE DRAWINGS

A further understanding of the nature and advantages of the present invention may be realized by reference to the remaining portions of the specification and the drawings, wherein like reference numerals are used throughout the several drawings to refer to similar components. In some instances, a sublabel is associated with a reference numeral and appended to the reference numeral with a hyphen to denote one of multiple similar components. When reference is made to a reference numeral without specification to an existing sublabel, it is intended to refer to all such multiple similar components.

DETAILED DESCRIPTION OF THE INVENTION

1. Overview

Figure 1A:
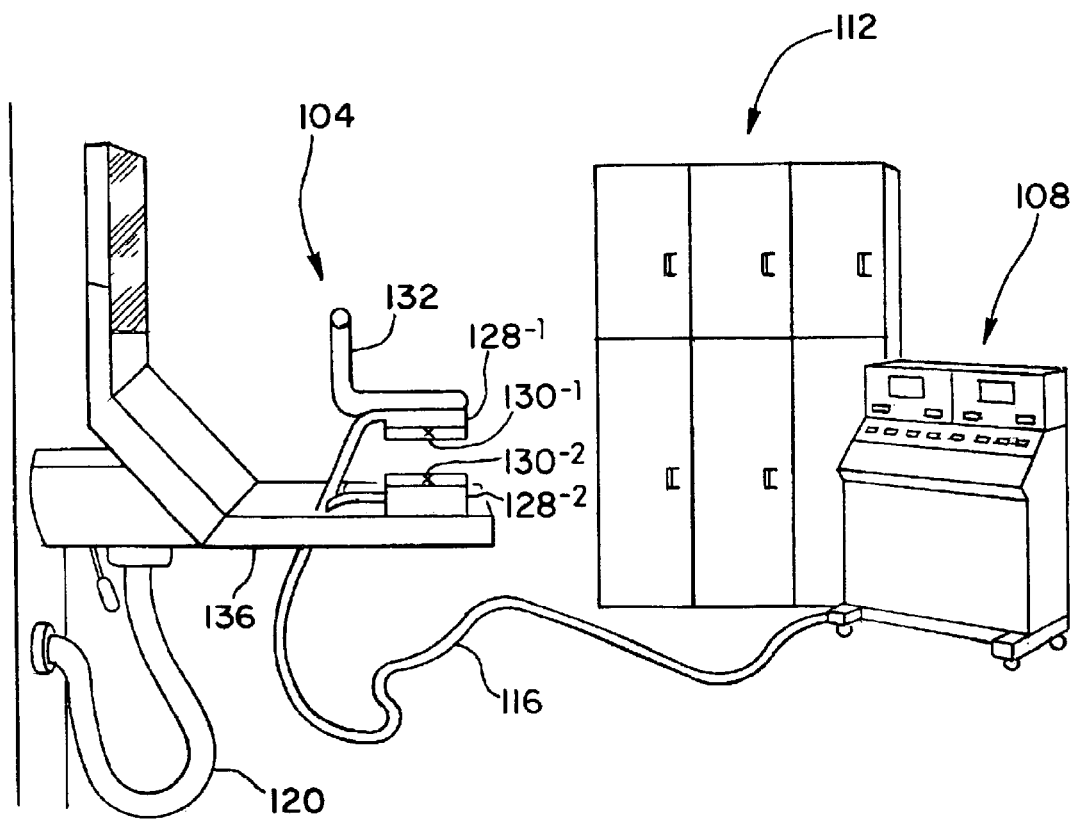
FIGS. 1A and 1B provide an overview of a system according to one embodiment of the invention, illustrated as a physical embodiment in FIG. 1A and illustrated schematically in FIG. 1B.
Figure 1B:
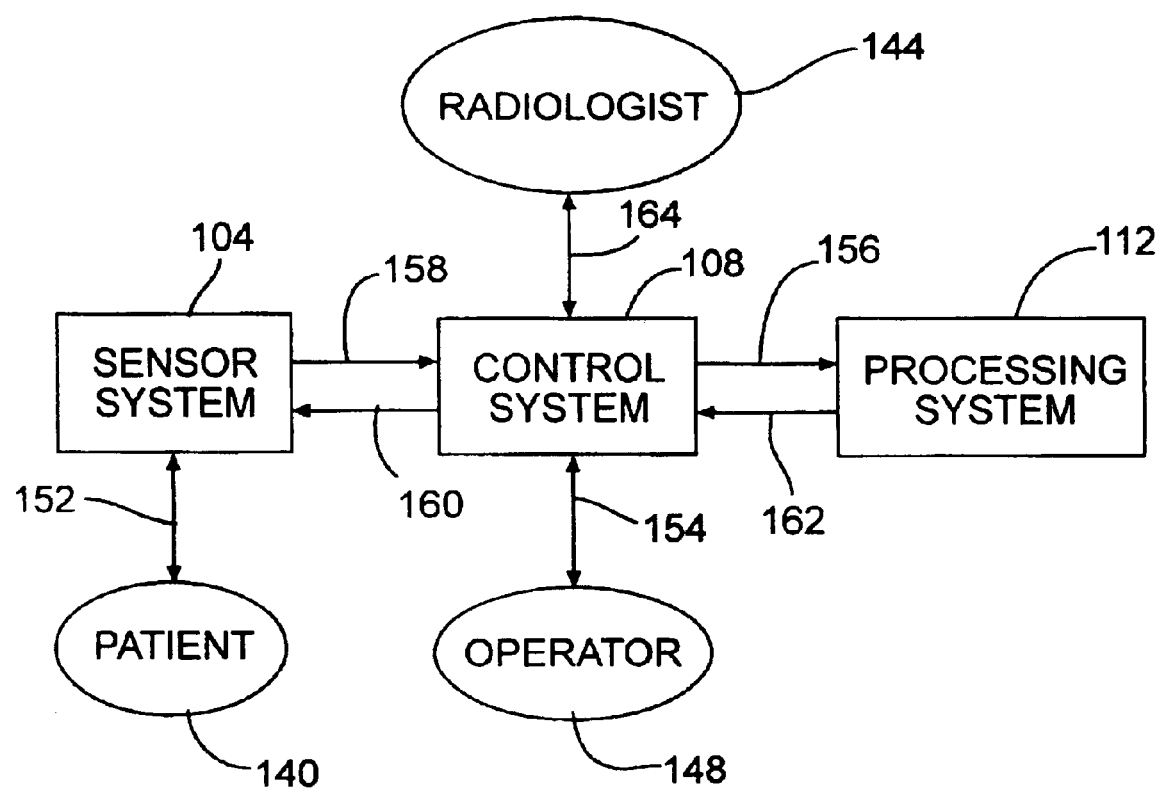

Embodiments of the invention are directed generally to a method and apparatus for examining an object under study, such as tissue. FIGS. 1A and 1B provide a general structural overview of a system that may be configured according to an embodiment of the invention appropriate for medical applications, particularly for ultrasound imaging of a patient's breast. While FIG. 1A shows the physical arrangement of the system components, FIG. 1B shows the logical interconnection of those components and how individuals interact with the system.

The system includes a sensor system 104, a control system 108, and a processing system 112. Each of these systems is described in greater detail in the following commonly assigned patents and applications, the entire disclosures of all of which are herein incorporated by reference for all purposes: U.S. Pat. No. 6,385,474 entitled "METHOD AND APPARATUS FOR HIGH-RESOLUTION DETECTION AND CHARACTERIZATION OF MEDICAL PATHOLOGIES," filed Mar. 19, 1999 by John D. Rather et al., which is a nonprovisional of U.S. Prov. Pat. Appl. No. 60/078,788 entitled "HIGH RESOLUTION ULTRASOUND ANATOMICAL IMAGING SYSTEM," filed Mar. 20, 1998 by John D. Rather; U.S. patent application Ser. No. 10/323,354 entitled "COMPUTERIZED ULTRASOUND RISK EVALUATION SYSTEM," filed concurrently with this application by Neb Duric et al.; and U.S. patent application Ser. No. 10/323,467 entitled "DIAGNOSTIC ANALYSIS OF ULTRASOUND DATA," filed concurrently with this application by David H. Chambers et al.

A connection 116 is provided for the transfer of information between the sensor system 104 and the control system 108 and a connection (not shown in FIG. 1A) is provided for the transfer of information between the control system 108 and the processing system 112. In some embodiments, such connections may comprise, for example, ethernet connections.

In some embodiments, the sensor system 104 might comprise acoustic transmission and acoustic receiving elements: Insonification may be achieved with acoustic transmission elements and scattered acoustic information may be received with acoustic receiving elements. In one embodiment, the acoustic transmission elements and the acoustic receiving elements are configured as one or more arrays and are comprised by a paddle. The arrays may be configured for motion to allow the field to be scanned. In one embodiment, the paddle also comprises a pliable bladder configured for contacting the tissue to improve the level of comfort of the patient and to examine regions otherwise difficult to access. The pliable bladder may contain an acoustically transparent liquid. In some embodiments, a second similarly configured paddle may be provided so that scanning of the tissue may be performed by moving arrays of transmission and receiving elements in the separate paddles in parallel.

In the embodiment shown, the sensor system 104 includes a support 136, a source for power connections 120, and a sensor that includes a pair of paddles 128. The lower paddle 128-2 is fixed to the support 136, but the upper paddle 128-1 is configured to be moved with a handle 132 to compress the patient's breast between the two paddles 128. Each of the paddles 128 comprises arrays of ultrasonic transmission and receiving elements ("transducers"). In one embodiment, 512 transmission elements and 512 receiving elements are provided in each paddle. Included in the sensor system are one or more registration fiducials 130. It should be noted that registration fiducials can be any objects or marks within the insonification field that can be measured with or identified by acoustic radiation. For example, in the present embodiment, the registration fiducials 130 are markers implanted into the paddles 128, such that the registration fiducials are included in the insonification field produced by the transducers.

The control system 108 comprises hardware used to form and time ultrasonic transmission pulses and circuitry that records the received ultrasonic information. The operator 148 operates the control system 108 via interaction 154. In operation, the patient 140 has an interaction 152 with the sensor system 104 by being positioned so that the paddles 128 are contacting the patient's breast. The operator 148 has an interaction 154 with the control system 108 to set up the operational parameters. In one embodiment, the control system 108 is configured to provide a graphical user interface from which operational parameters such as mode selection and timing initiation may be established. The control system 108 derives control information from the instructions provided by the operator 148.

Once the operation mode has been established, the control system 108 directs the sensor system 104 to begin acquiring data via interaction 160. The sensor, shown as paddles 128 in the illustrated embodiment, insonifies a field, the field including the tissue (not shown) and the registration fiducials 130, and receives acoustic information scattered from the field. Scattered acoustic information can be any acoustic radiation received by the sensor system that contains information about objects in the field. For example, in certain embodiments, scattered acoustic information is acoustic radiation reflected by, refracted by or transmitted through the objects in the field. In some embodiments, scattered acoustic information is some combination of transmitted and reflected acoustic information.

Transducers within the paddles 128 convert the received acoustic information into electrical signals that are communicated back to the control system 108 through interaction 158. The control system 108 performs an analysis of the electrical signals to create a data set that is transmitted via interaction 156 to the processing system 112. The processing system generates a representation of the field, the representation including a depiction of the registration fiducials 130 as well as the tissue, and processes the representation based on the depiction of the registration fiducials 130.

The processed representation may then be transmitted to the control system 108 through interaction 156. A professional evaluator 144, such as a radiologist, may have a direct interaction 164 with the operator system 112 to view the representation. In alternative embodiments, selected representations may be printed or stored for later viewing and analysis by the evaluator 144.

Figure 2:
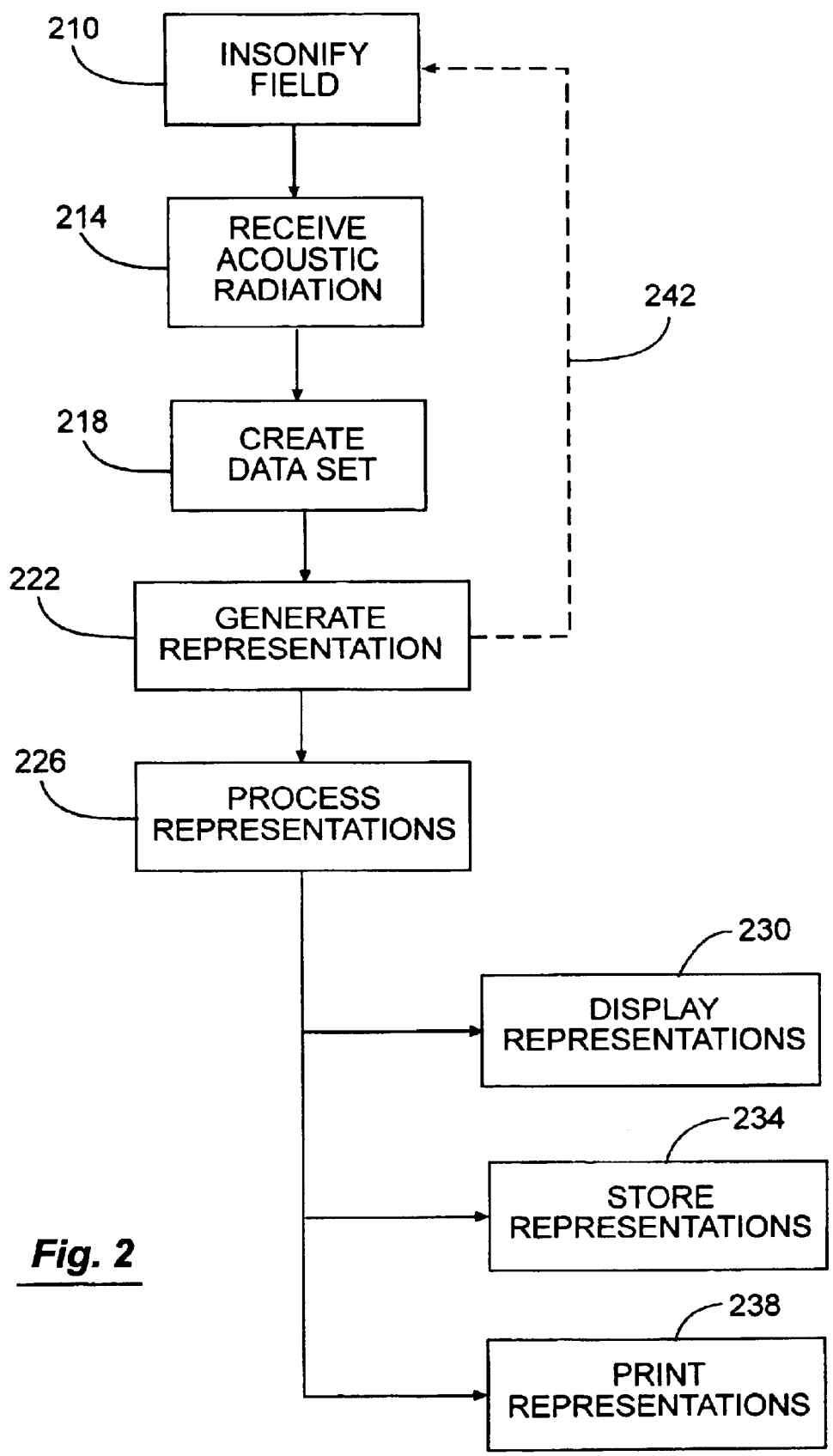
FIG. 2 provides a flow diagram in accordance with one embodiment of the invention.

FIG. 2 provides a flow diagram of one embodiment of the invention. First, the tissue is insonified at block 210 and acoustic radiation is received by the sensor system 104 at block 214. As described above, in some embodiments, the received radiation can be a mix of reflected and transmitted acoustic waves; in others, only reflected or only transmitted acoustic information might be received. Next, the control system creates a data set at block 218 from the received acoustic radiation. In some embodiments, creation of a data set may involve some amount of preprocessing, for instance reducing the amount of data collected by limiting the bandwidth of the data or limiting the number of data samples. At block 222, the processing system derives a representation from the data set. In certain embodiments, a plurality of representations may be generated by the method described herein, as indicated by line 242. In some embodiments, the representation may be an image. In others, it may be three dimensional, or it may be a tomographic slice.

A tomographic "view" is defined by data generated for transmission of acoustic radiation from a single transmission element and reception by a plurality of the receiving elements. A tomographic "slice" is defined by data generated for a plurality of views, i.e. derived from transmission of acoustic radiation from a plurality of transmission elements and reception by a plurality of receiving elements.

In block 226, the processing system 112 processes the representations to correlate the depicted properties of the registration fiducials with the fiducials' actual properties. By way of example, as described below, in certain embodiments, the registration fiducials are objects with known acoustic properties. Such properties may include sound speed, attenuation, density, compressibility, acoustic impedance change, and the like. After the representation is derived from the data set, the representation can be calibrated with reference to the object of known acoustic properties. For instance, if the object has a known sound speed, the representation can be adjusted so that the represented sound speed of the object corresponds to the known sound speed for that object. Thus calibrated, the representation will more accurately depict the sound speed of the tissue insonified, enabling more accurate examination of the tissue. In other embodiments, the registration fiducials might comprise a plurality of objects with known acoustic properties.

Finally, in certain embodiments, the representations may be displayed to the operator or radiologist as shown in block 230, stored for later recall as shown in block 234, or printed as shown in block 238. The control system coordinates each function in communication with the sensor system and the processing system by defining setup conditions for each function and determining when each function is complete.

2. Fiducial Object for Iterative Processing

Figure 3A:
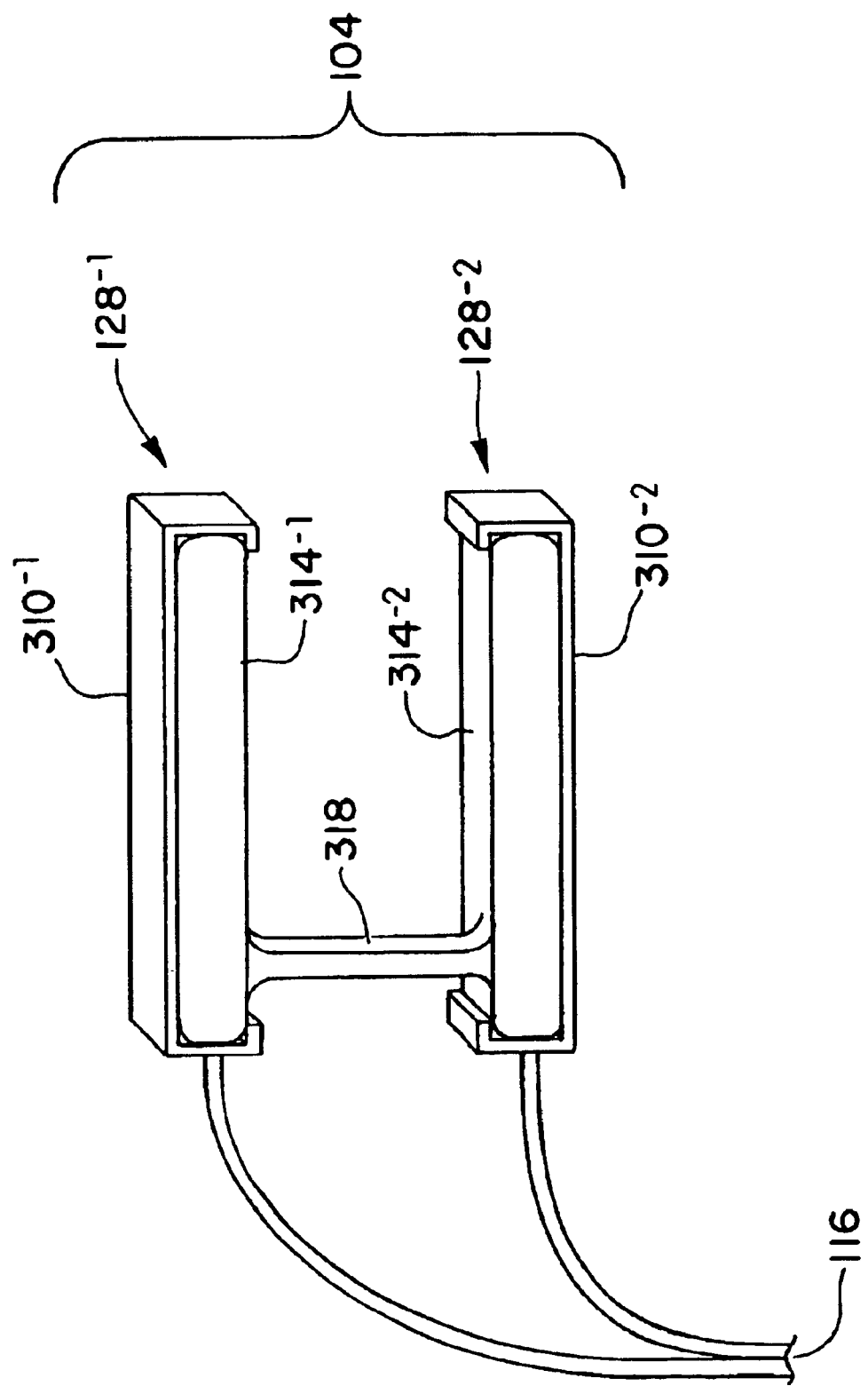
FIG. 3A provides a perspective drawing of a sensor system configured with a fiducial object of known acoustic properties, in accordance with an embodiment of the invention.
Figure 3B:
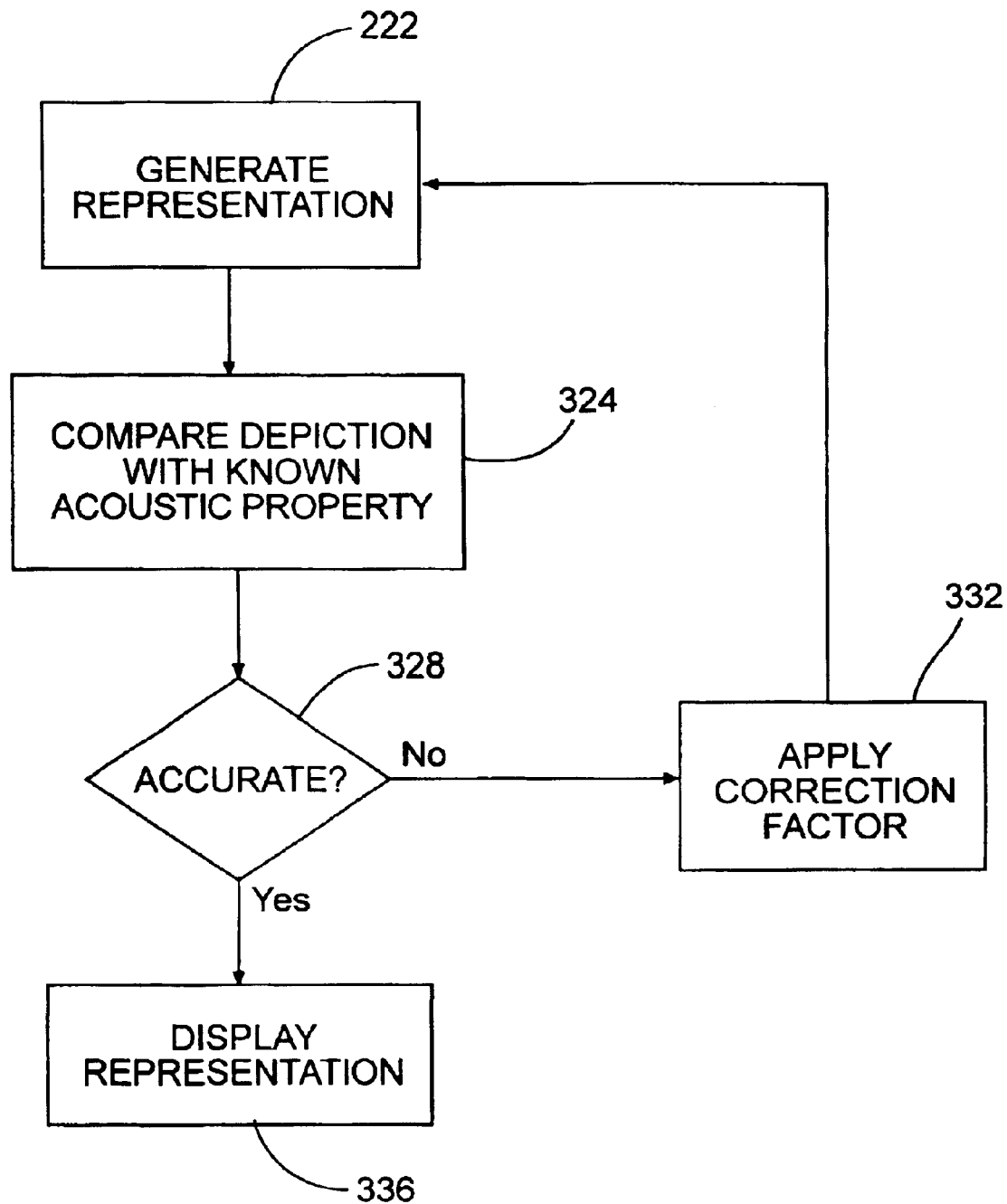
FIG. 3B provides a flow diagram, wherein a derived representation is calibrated with respect to known acoustic properties of a fiducial object, in accordance with the embodiment illustrated in FIG. 3A.

FIGS. 3A and 3B illustrate another embodiment of the invention. FIG. 3A provides a perspective drawing of a sensor system utilizing a fiducial object of known acoustic properties. The sensor system 104 communicates with a control system (not shown in FIG. 3A) via a connection 116. In this embodiment, the sensor system 104 further comprises a pair of acoustic paddles 128, but in other embodiments the sensor system 104 might comprise only one paddle; those skilled in the art will recognize that many other implementations may be devised to perform the insonification. Each acoustic paddle 128 comprises an enclosure 310, the enclosure comprising a transducer array (not shown in FIG. 3A) and an acoustic transmission medium (not shown in FIG. 3A). Each paddle further comprises a pliable coupling bladder 314. Situated between the pliable coupling bladders 314 is a registration fiducial; in this embodiment, the registration fiducial is a fiducial object 318 with known acoustic properties.

FIG. 3B describes the iterative processing of a representation produced by the embodiment of FIG. 3A. Referring now to FIGS. 2 and 3A, a field is insonified at block 210 by the sensor system 104. At block 214, scattered acoustic information is received. In this embodiment, the received acoustic information includes some acoustic information scattered by the fiducial object 318. From this information, a data set is created at block 218. At block 222, the processing system generates a representation of the insonified field, including a depiction of the fiducial object 318. There are several ways of reconstructing a representation of an insonified field including, among others, those described in U.S. patent application Ser. No. 10/323,467 entitled "DIAGNOSTIC ANALYSIS OF ULTRASOUND DATA," filed concurrently with this application by David H. Chambers et al., which has been incorporated by reference in its entirety.

Referring back now to FIG. 3B, after the representation is generated at block 222, the processing system compares the depicted acoustic properties of the fiducial object with the object's corresponding known properties at block 324. In certain embodiments, if the processing system determines that the depicted properties match the object's known properties to within a predefined tolerance, as shown at block 328, the processing system transmits the representation back to the control system for display to the operator. Those skilled in the art will recognize, however, that the representation could be managed in other ways, for example, printed, stored for future reference or the like.

In the present embodiment, if the depicted properties of the object do not match its known properties, the processing system calculates a correction factor at block 332 and uses that correction factor to generate a corrected representation at block 222. A correction factor is any set of one or more coefficients or algorithms that, when applied to a data set or representation, will allow the resulting representation to conform more closely with the actual objects represented. In this embodiment, for example, the correction factor might be derived with a set of curve-fitting algorithms that correlate a range of measured values of a fiducial object's acoustic properties with the object's known, actual properties. Thus, the process iterates until the depicted properties of the fiducial object match the known properties thereof to within a predetermined tolerance, as shown at block 328. At that point, as discussed above, the representation can be displayed to the operator at block 336, or in other embodiments, printed, stored for future reference or the like. Notably, the correction factor that produces an accurate depiction of the fiducial object's acoustic properties applies equally well to the rest of the representation and therefore can be used to correct the depiction of an unknown object, for instance, a patient's tissue.

In the embodiment illustrated by FIG. 3A, the fiducial object 318 is situated between two acoustic paddles 128. In other embodiments, the fiducial object might instead be placed between the unknown object and a first paddle, such that transmitted acoustic waves would pass through the fiducial object and the unknown object before being received by receiving elements in a second paddle; acoustic information scattered by the fiducial object and the unknown object would be received by receiving elements in the first paddle. Alternatively, some embodiments might employ only one paddle. In such embodiments, the fiducial object might be situated between the paddle and the unknown object; acoustic radiation transmitted by transmitting elements in the paddle would be reflected by the fiducial object and the unknown object; the scattered acoustic information would then be received by receiving elements in the same paddle. After reviewing the foregoing description, those skilled in the art will recognize that other configurations of paddles, known objects and unknown objects are possible as well.

3. Positional Correlation of Fiducial Markers

Figure 4A:
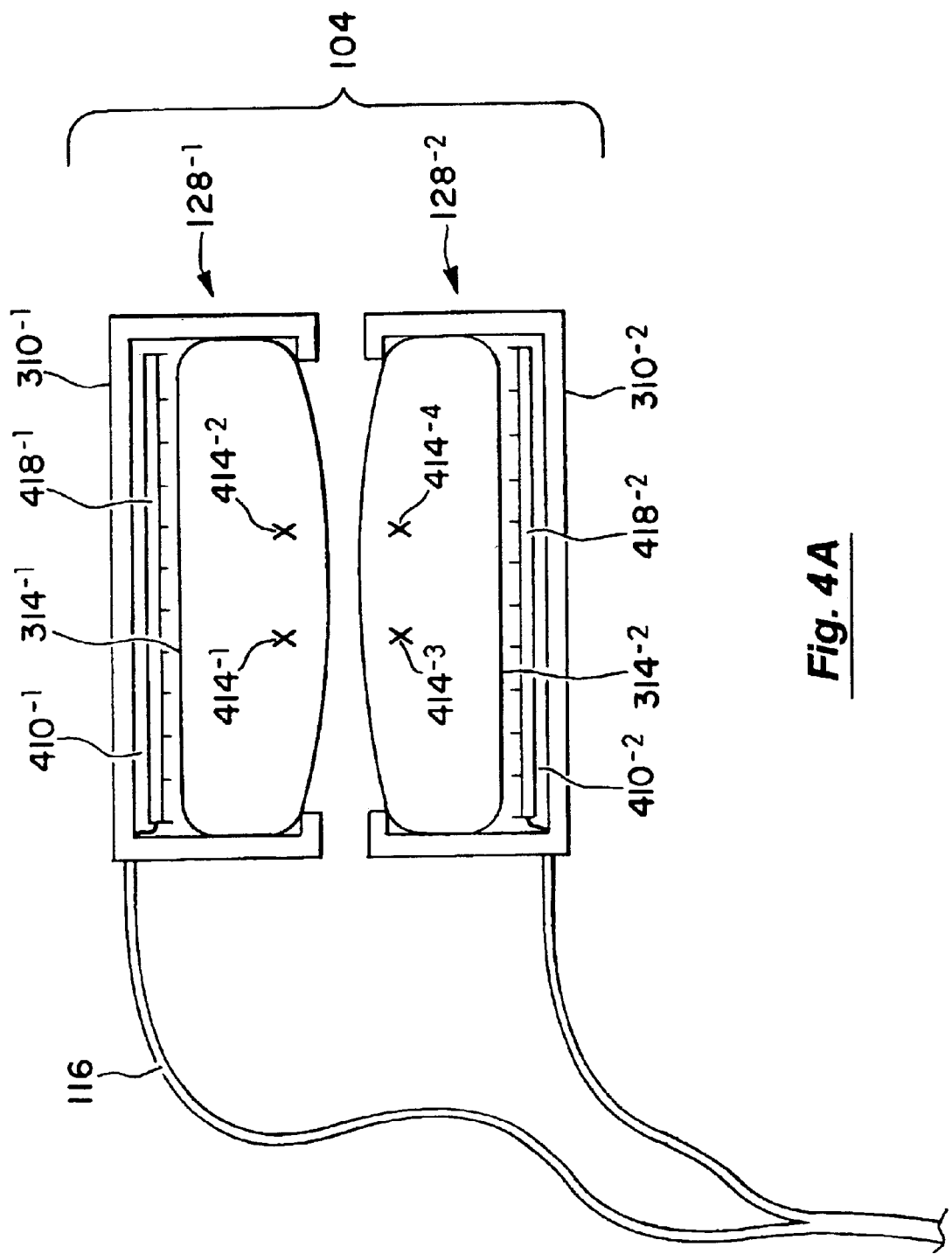
FIG. 4A provides a sectional drawing showing a sensor system configured with a plurality of fiducial markers in accordance with an embodiment of the invention.

FIG. 4A is a sectional drawing of a sensor system 104 in accordance with another embodiment of the invention. The sensor system 104 communicates with a control system (not shown in FIG. 4A) via a connection 116. In this embodiment, the sensor system 104 comprises a pair of acoustic paddles 128, but in other embodiments the sensor system might comprise only one paddle, or might use a different apparatus to perform the insonification. Each acoustic paddle 128 comprises an enclosure 310, the enclosure comprising a transducer array 410 and an acoustic transmission medium 418. Each acoustic paddle further comprises a pliable coupling bladder 314. Embedded in each of the coupling bladders 314 is a plurality of registration fiducials. In this embodiment, the registration fiducials comprise fiducial markers 414.

Figure 4B:
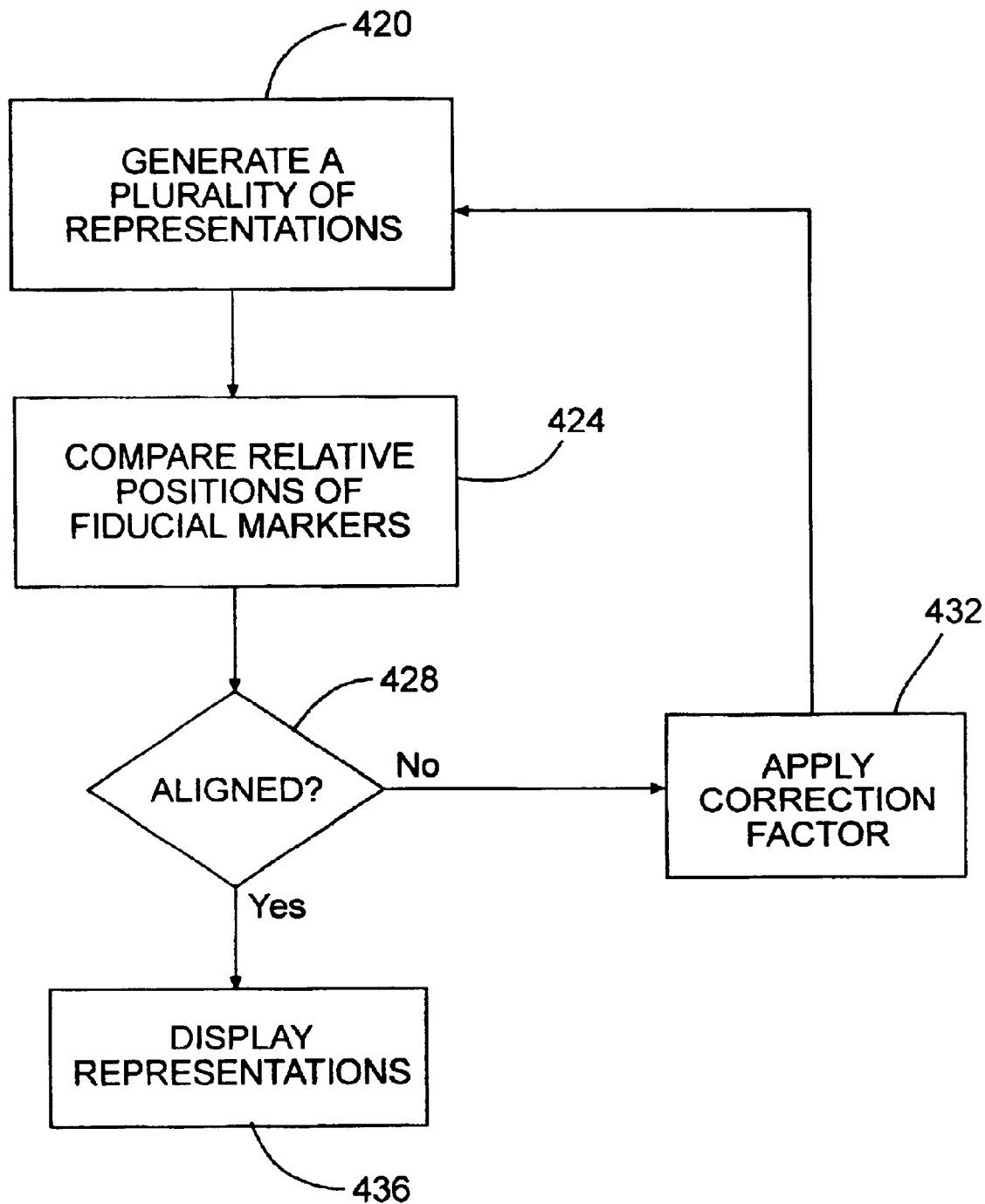
FIG. 4B provides a flow diagram, wherein the relative positions of fiducial markers in a plurality of representations are correlated to localize a feature of the examined tissue, in accordance with the embodiment illustrated in FIG. 4A.

FIG. 4B provides a flow diagram illustrating the processing of multiple representations, in accordance with this embodiment. Referring now to FIGS. 2 and 4A, a field, including the tissue to be examined (not shown) and the fiducial markers 414, is insonified at block 210 and acoustic radiation is received at block 214. Fiducial markers 414 can be any low-contrast objects or marks capable of detection by acoustic imaging. In the present embodiment, the fiducial markers 414 comprise plastic crosses embedded in the coupling bladders. In some embodiments, the fiducial markers 414 might comprise other materials in a variety of shapes and configurations. In other embodiments, the fiducial markers 414 might not be embedded in the pliable coupling bladder 314 but instead might be fixedly attached to the object to be examined; alternatively, the fiducial markers 414 might otherwise be situated in the insonification field, so long as their position is fixed. After the acoustic radiation is received at block 214, a data set is created from the received information at block 218. From the data set, a representation is generated at block 222.

FIG. 4B is a flow diagram illustrating the processing of a plurality of representations in accordance with the embodiment of FIG. 4A. First, at block 420, a plurality of representations are generated by the method described above. In certain embodiments, the plurality of representations are generated over a period of time, perhaps multiple hours, days, weeks, months or years, such that the representations allow comparative analysis of the examined tissue over time. The relative positions of the fiducial markers 414 in the plurality of representations are compared at block 424. If the relative positions of the fiducial markers are not aligned in each of the representations to within a predetermined tolerance, as shown in block 428, a correction factor is applied to one or more of the data sets or representations in order to more closely correlate the relative positions of the fiducial markers 414, and corrected representations are generated at block 420. In the illustrated embodiment, the correction factor might be positional in nature; for instance, the correction factor might be an offset that adjusts an image representation by several pixels in a certain direction, so that the representation is aligned with other representations. Alternatively, the correction factor might translate or rotate a representation in one or more dimensions to correlate the relative positions of the fiducial markers. Thus, the process iterates until the relative positions of the fiducial markers are correlated to within a predetermined tolerance.

According to the present embodiment, after the relative positions of the fiducial markers have been correlated, the representations are displayed at block 436. In some embodiments, however, the representations might be printed, stored for future reference, or the like. In other embodiments, the representations might be superimposed upon one another to allow for comparative analysis of the plurality of representations.

One benefit of the illustrated embodiment is that, by correlating the relative positions of the fiducial markers, a feature within the tissue can be localized in each of the representations. One possible application of such an embodiment is to allow the tissue to be examined a plurality of times—perhaps over a span of multiple days, weeks, months or years—creating multiple representations. By correlating the depictions of the fiducial markers, a feature of the tissue can be localized in each representation. In this way, any change in the feature over time can be tracked and studied from a consistent frame of reference. Where, for instance, the feature is a cancerous tumor, such localized representations could allow medical practitioners more precisely to determine the growth of the tumor or, alternatively, the tumor's response to treatment.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A method for examining tissue, the method comprising:
   contacting a tissue with a first paddle, the first paddle comprising:
      a first pliable bladder containing a first acoustically transparent liquid; and
      a first array of acoustic transmission and acoustic receiving elements;
   insonifying a field with acoustic waves, wherein the field includes a portion of the tissue and at least one registration fiducial;
   receiving scattered acoustic information from the field to produce a data set; and
   generating a representation of the portion of the tissue from the data set, the representation including a depiction of the at least one registration fiducial.

2. The method of claim 1, wherein the at least one registration fiducial comprises at least one object having a known acoustic property.

3. The method of claim 2, wherein the known acoustic property is selected from the group consisting of sound speed, attenuation, density, compressibility and acoustic impedance change.

4. The method of claim 2, further comprising calibrating the representation to correlate the depiction of the at least one registration fiducial to the known acoustic property.

5. The method of claim 1, wherein the at least one registration fiducial comprises a plurality of fiducial markers.

6. The method of claim 5, wherein the representation comprises a plurality of representations, the method further comprising correlating relative positions of the plurality of fiducial markers from the plurality of representations to localize a feature of the portion of the tissue.

7. The method of claim 6, wherein the feature is a cancerous tumor.

8. The method of claim 1, wherein the representation is an image.

9. The method of claim 1, wherein the representation is a three dimensional representation.

10. The method of claim 1, wherein the representation is a two dimensional tomographic slice through the portion of the tissue.

11. The method of claim 1, wherein the data set is produced from transmitted and reflected acoustic information.

12. The method of claim 1, wherein insonifying the field further comprises contacting the tissue with a second paddle, the second paddle comprising:
   a second pliable bladder containing a second acoustically transparent liquid; and
   a second array of acoustic transmission and acoustic receiving elements.

13. A system for examining tissue, the system comprising:
   a sensor system, the sensor system including:
      a plurality of acoustic transmission elements disposed to surround at least a portion of the tissue;
      a plurality of acoustic receiving elements disposed to surround at least a portion of the tissue; and
      at least one registration fiducial;
   a control system in communication with the sensor system, the control system comprising a controller for controlling the acoustic transmission elements and the acoustic receiving elements to insonify a field with acoustic waves and to receive scattered acoustic information from the field to produce at least one data set, wherein the field includes at least a portion of the tissue and the at least one registration fiducial; and
   a processing system in communication with the control system, the processing system comprising a processor adapted for generating a representation of the portion of the tissue from the at least one data set, the representation including a depiction of the at least one registration fiducial.

14. The system of claim 13, wherein the sensor system further includes a first paddle, the first paddle comprising:
   a first pliable bladder containing a first acoustically transparent liquid; and
   a first array of acoustic transmission and acoustic receiving elements.

15. The system of claim 14, wherein the sensor system further includes a second paddle, the second paddle comprising:
   a second pliable bladder containing a second acoustically transparent liquid; and
   a second array of acoustic transmission and acoustic receiving elements.

16. The system of claim 13, wherein:
   the at least one registration fiducial comprises at least one object having a known acoustic property; and
   the processor is further adapted for calibrating the representation to correlate the depiction of the at least one registration fiducial to the known acoustic property.

17. The system of claim 16, wherein the known acoustic property is selected from the group consisting of sound speed, attenuation, density, compressibility and acoustic impedance change.

18. The system of claim 13, wherein:
   the at least one registration fiducial comprises a plurality of fiducial markers; and
   the processor is adapted for generating a plurality of representations of the portion of the tissue from the at least one data set, and for correlating relative positions of the plurality of fiducial markers from the plurality of representations to localize a feature of the portion of the tissue.

19. The system of claim 18, wherein the feature is a cancerous tumor.

20. The system of claim 13, wherein the representation is an image.

21. The system of claim 13, wherein the representation is a three dimensional representation.

22. The system of claim 13, wherein the representation is a two dimensional tomographic slice through the portion of the tissue.

23. The system of claim 13, wherein the data set is produced from transmitted and reflected acoustic data.

24. A computer-readable storage medium having a computer-readable program embodied therein for directing operation of a tissue imaging system including a sensor system and a processing system, wherein the computer-readable program includes instructions for operating the tissue imaging system to examine tissue in accordance with the following:
   insonifying a field with a plurality of acoustic transmission elements comprised by the sensor system, wherein the field contains a portion of the tissue and at least one registration fiducial;
   receiving scattered acoustic information from the field with a plurality of acoustic receiving elements comprised by the sensor system to produce a data set; and
   generating a representation of the portion of the tissue from the data set with the processing system, the representation including a depiction of the at least one registration fiducial.

25. The computer-readable storage medium of claim 24, wherein:
   the at least one registration fiducial comprises at least one object having a known acoustic property; and
   the computer-readable program further includes instructions for calibrating the representation to correlate the depiction of the at least one registration fiducial to the known acoustic property.

26. The computer-readable storage medium of claim 24, wherein:
   the at least one registration fiducial comprises a plurality of fiducial markers;
   the representation comprises a plurality of representations; and
   the computer-readable program further includes instructions for correlating relative positions of the fiducial markers from the plurality of representations to localize a feature of the portion of the tissue.

27. A system for examining tissue, the system comprising:
   a sensor system comprising:

means for providing a fiducial reference;

means for transmitting acoustic radiation to a field, wherein the field contains the means for providing a fiducial reference and a portion of the tissue; and means for receiving acoustic information scattered from the field to produce a data set;

means for controlling the sensor system to insonify the field with acoustic waves and to receive scattered acoustic information from the field; and means for processing the received acoustic information to produce a representation of the field from the data set, wherein the representation includes a depiction of the means for providing a fiducial reference.

28. The system of claim 27, wherein the representation comprises a plurality of representations, the system further comprising means for correlating relative positions of the means for providing a fiducial reference in the plurality of representations to localize a feature of the portion of the tissue.

29. The system of claim 27, wherein the means for providing a fiducial reference has a known acoustic property, the system further comprising means for calibrating the representation to correlate the depiction of the means for providing a fiducial reference to the known acoustic property.

30. The system of claim 29, wherein the known acoustic property is selected from the group consisting of sound speed, attenuation, density, compressibility and acoustic impedance change.

* * * * *